United States Patent
Dienst et al.

(10) Patent No.: US 8,323,291 B2
(45) Date of Patent: Dec. 4, 2012

(54) PARTIAL AIMING DEVICE FOR TARGETING AN ARTHROSCOPIC OPERATION SITE FOR A MEDICAL INTERVENTION

(75) Inventors: Michael Dienst, Homburg (DE); Sascha Berberich, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 909 days.

(21) Appl. No.: 11/829,440

(22) Filed: Jul. 27, 2007

(65) Prior Publication Data

US 2008/0027457 A1    Jan. 31, 2008

(30) Foreign Application Priority Data

Jul. 27, 2006   (DE) .......................... 10 2006 035 579

(51) Int. Cl.
    *A61B 17/56*          (2006.01)
(52) U.S. Cl. ........................... 606/96; 606/88
(58) Field of Classification Search ............... 606/87–88, 606/96–98; 623/18.11, 19.11–19.14, 20.11–20.17, 623/22.11–22.12
See application file for complete search history.

(56) References Cited

U.S. PATENT DOCUMENTS

| | | | | |
|---|---|---|---|---|
| 4,722,331 A | * | 2/1988 | Fox .................................. | 606/96 |
| 4,781,182 A | * | 11/1988 | Purnell et al. .................... | 606/96 |
| 4,784,126 A | | 11/1988 | Hourahane | |
| 5,163,940 A | * | 11/1992 | Bourque .......................... | 606/96 |
| 5,269,786 A | | 12/1993 | Morgan ........................... | 606/96 |
| 5,458,602 A | * | 10/1995 | Goble et al. ..................... | 606/96 |
| 5,562,664 A | * | 10/1996 | Durlacher et al. ............... | 606/96 |
| 5,688,284 A | * | 11/1997 | Chervitz et al. ................. | 606/96 |
| 6,254,606 B1 | * | 7/2001 | Carney et al. .................. | 606/102 |
| 6,342,056 B1 | * | 1/2002 | Mac-Thiong et al. .......... | 606/96 |
| 6,565,550 B1 | * | 5/2003 | Klein et al. ..................... | 604/506 |
| 2003/0065391 A1 | * | 4/2003 | Re et al. ...................... | 623/13.14 |
| 2004/0193172 A1 | * | 9/2004 | Ross et al. ....................... | 606/96 |
| 2006/0069394 A1 | | 3/2006 | Weiler et al. .................... | 606/96 |

FOREIGN PATENT DOCUMENTS

| | | |
|---|---|---|
| DE | 3436253 A1 | 7/1985 |
| DE | 196 18 354 | 11/1997 |
| DE | 200 19 026 | 3/2002 |
| DE | 10 2004 048 042 | 4/2006 |
| GB | 2230453 A | 10/1990 |

OTHER PUBLICATIONS

Dizioglu, B and K Lakshiminarayana. "Mechanics of Form Closure." Acta Mechanica 1984 107-118. Web. May 18, 2009.*

* cited by examiner

*Primary Examiner* — Kevin T Truong
*Assistant Examiner* — Larry E Waggle, Jr.
(74) *Attorney, Agent, or Firm* — St. Onge Steward Johnston & Reens LLC

(57) ABSTRACT

A partial aiming device for targeting an arthroscopic operation site for a medical intervention has a circularly arcuate element and with a first, radially extending aiming rod which can be moved along the circularly arcuate element. It is proposed that on the circularly arcuate element there is a connecting device by means of which a medical instrument with a shaft can be connected to the partial aiming device in such a way that the shaft is orientated as a second aiming rod that extends radially towards the first aiming rod.

6 Claims, 5 Drawing Sheets

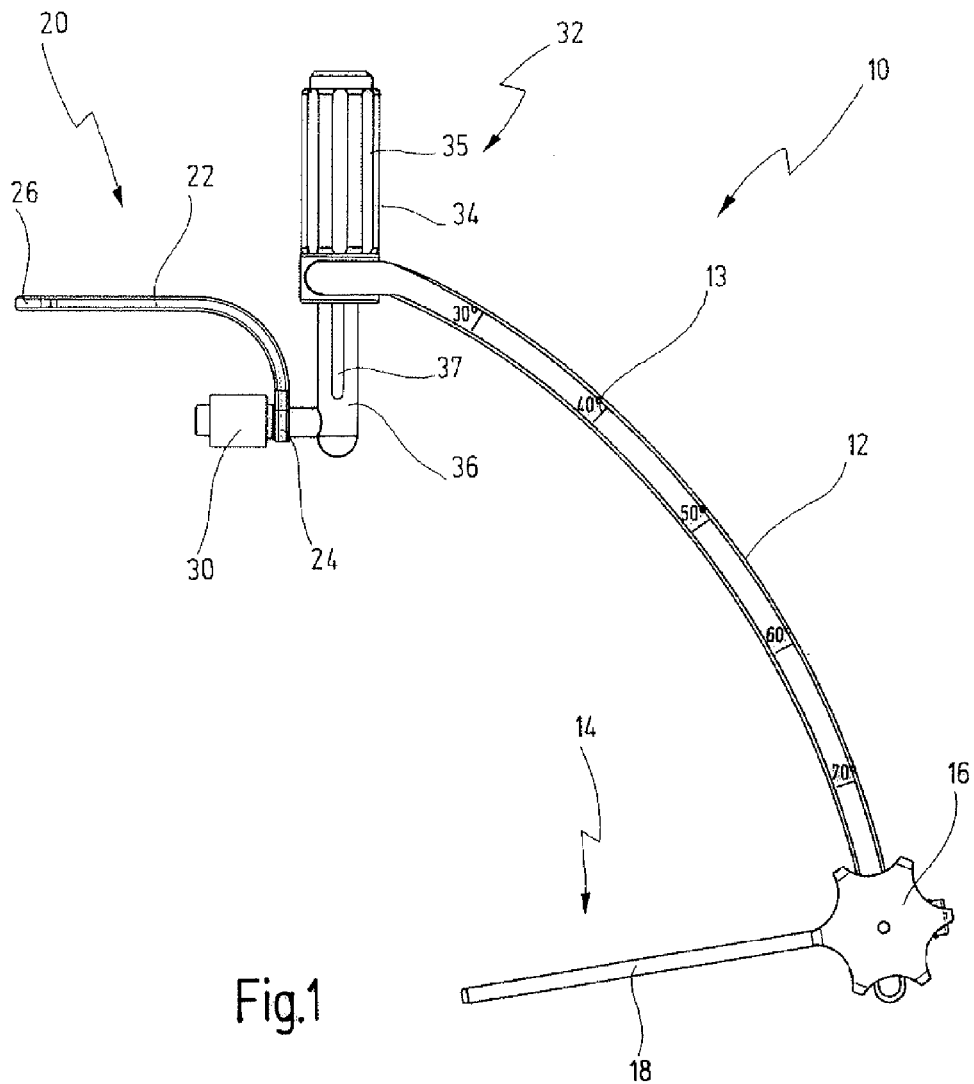
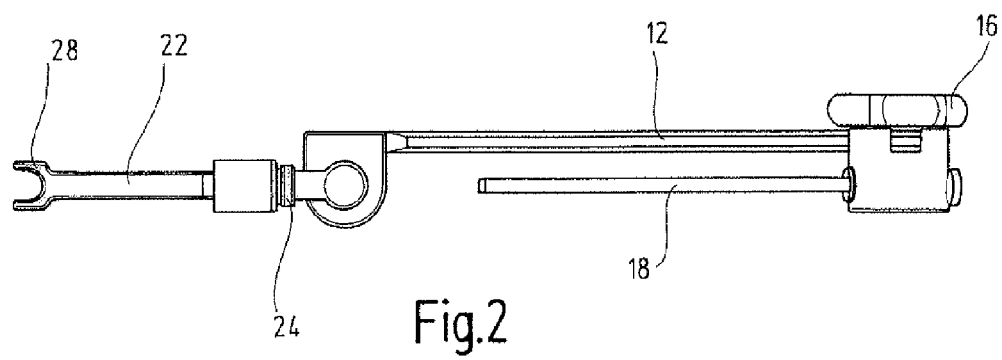

PARTIAL AIMING DEVICE FOR TARGETING AN ARTHROSCOPIC OPERATION SITE FOR A MEDICAL INTERVENTION

BACKGROUND OF THE INVENTION

The invention relates to a partial aiming device for targeting an arthroscopic operation site for a medical intervention.

A complete aiming device is known from DE 196 18 354 C2.

Such aiming devices are used in the medical field to target a non-visible operation site for an arthroscopic investigation or a surgical intervention. Arthroscopy or the visualization of joints is a minimally invasive surgical intervention that can be used for diagnosis, e.g. for investigation of the state of cartilages and ligaments, and/or for treatment, e.g. removal of the meniscus, cartilage shaving, etc.

During an arthroscopic investigation or an arthroscopic intervention, the joint, for example the knee joint, is examined from the inside. An arthroscope is introduced into the joint cavity through a small incision in the skin. Using the arthroscope, which has an optical system, it is possible to inspect the structures of the joint. The arthroscope can also be connected to a camera that transfers images to a monitor.

To move the arthroscope to the requisite joint site, which is not visible to the surgeon, aiming devices of the above kind are used.

The device known from DE 196 183 54 CZ has a circularly arcuate element, on which there is a first aiming rod which can be moved along the circularly arcuate element. The longitudinal axis of the first aiming rod extends along a radius or a diameter of the circle along which the circularly arcuate element extends.

The circularly arcuate element also has attached to it a second aiming rod formed as a tube. The longitudinal axis of the second aiming rod also extends along a radius or a diameter of the circle along which the circularly arcuate element extends.

The longitudinal axes of the first and second aiming rods intersect in approximately the area of the operation site.

For arthroscopy of the knee, the tip of the first aiming rod is applied to one side of the knee from the outside in such a way that it is at roughly the intended exit point of the extension of the tube of the second aiming rod.

The tube, which is likewise connected to the arcuate element, is then applied on the opposite side. In this way the doctor can see, from the outside, the direction in which the arthroscopic instrument will be introduced into the knee joint through the tube. The first and second aiming rods are applied firmly on the opposing sides according to the desired orientation, and held in this position by means of the arcuate element.

The instrument can now be accurately introduced into the joint through the tube of the second aiming rod, and the intervention or investigation performed.

The aiming device remains on the body throughout the intervention. The aiming device is a cumbersome instrument that is needed only for the purposes of targeting and not for the actual intervention or the investigation. The cumbersome device gets in the way in the area around the joint.

It is therefore an object of the invention to create a device which enables the operating site to be targeted precisely but which does not get in the way of the actual intervention or the investigation.

SUMMARY OF THE INVENTION

This object is achieved by a partial aiming device for targeting an arthroscopic operation site for a medical intervention, comprising a circularly arcuate element, a first aiming rod extending radially from said circularly arcuate element, said first aiming rod can be moved along said circularly arcuate element, a connecting device arranged at said circularly arcuate element, said connecting device is designed for connecting a medical instrument having a shaft in such a way at said circularly arcuate element that said shaft of said medical instrument extends radially from said circularly arcuate element too, said shaft being oriented by said connecting device as a second aiming rod that extends towards said first aiming rod.

The advantage of this measure is that the connecting device allows the arcuate element, together with the first aiming rod, to be connected to the medical instrument with which the actual arthroscopic investigation or the intervention is performed. For this purpose, this instrument has always a shaft which is employed as a second aiming rod of the aiming device when connected to the connecting device.

In this way it is possible to design the aiming device as a partial aiming device which consists of the arcuate element, the first aiming rod, and the connecting device and which can be attached to the instrument for the purposes of targeting.

This assembly then forms a complete aiming device comprising the arcuate element and the two aiming rods. The aiming device, now complete, can be applied to the joint, and the second aiming rod i.e. the shaft of the medical instrument—can accurately be introduced into the joint. Once the shaft of the medical instrument has been introduced into the joint, the connection between the connecting device and the medical instrument can be released and the partial aiming device can be removed, leaving only the medical instrument in the joint for the investigation or for the actual intervention. The area around the joint is thus no longer impeded by the cumbersome assembly formed by the arcuate element and the second aiming rod.

Targeting can thus be carried out very reliably in the usual manner as with a complete aiming device. The design as a partial aiming device means that, once the operation or investigation site has been targeted, the arcuate element and the first aiming rod, i.e. the actual structural elements that stick out in a cumbersome manner and get in the way, can be removed.

Thanks to the fact that the connecting device is designed in such a way that the shaft of the medical instrument attached to the connecting device extends radially towards the first aiming rod, this shaft can be used as a second aiming rod of the aiming device.

In a further embodiment of the invention, the connecting device is designed so that the latter can be attached to an existing connecting site of the medical instrument.

The advantage of this measure is that the partial aiming device according to the invention can be used with existing instruments. Adaptation of medical instruments to connect to the partial aiming device is thus avoided; the Latter has been adapted to the instrument instead.

In a further embodiment of the invention, the existing connecting site of the medical instrument is formed as a LUER connector.

This measure is advantageous because most of the medical instruments with which such investigations or interventions are carried out have a LUER connector, i.e. a connection in the form of a single thread, which is opened and closed by means of a half-turn. A LUER lock system, which is an internationally recognized standard connector, allows the partial aiming device to be compatible with instruments from various different manufacturers.

In a further embodiment of the invention, the connecting device has a bracing arm for supporting the partial aiming device at the medical instrument.

The advantage of this measure is that a connecting device of such a design ensures that the medical instrument sits stably on the partial aiming device according to the invention.

The additional support site results in that the attached medical instrument sits tilt-resistantly on the partial aiming device according to the invention during the targeting of an arthroscopic operation site.

In a further embodiment of the invention, a first end of the bracing arm is firmly connected to the connecting device.

The advantage of this measure is that the stability of the medical instrument on the partial aiming device according to the invention is increased.

In a further embodiment of the invention, a second end of the bracing arm can be brought against the medical instrument.

The advantage of this measure is that the second support site is easily effected, which means that it is still possible to easily separate the partial aiming device from the medical instrument.

In a further embodiment of the invention, a second end of the bracing arm can be brought against the medical instrument in such a way as to effect a form-closure.

The advantage of this measure is that bringing the second end of the bracing arm against the medical instrument in such a way as to effect a form-closure also produces a particularly stable connection and makes it easy to separate the medical instrument from the partial aiming device.

In a further embodiment of the invention, the connecting device is in addition provided with an adjusting device by means of which the connecting device can be moved axially in the direction of the shaft of the medical instrument.

The advantage of this measure is that the shaft of the medical instrument attached to the connecting device can be moved along its longitudinal axis. The placing of the shaft of the medical instrument on the joint can thus be optimized.

In a further embodiment of the invention, an angle between a longitudinal axis of the first aiming rod and a longitudinal axis of the shaft of the medical instrument is approximately 30° to 80°.

The advantage of this measure is that the aiming rods can be positioned within this angular range for the purposes of targeting.

In a further embodiment of the invention, the first aiming rod is formed as a tube.

The advantage of this measure is that another medical instrument, e.g. a puncture needle, can be introduced through the first aiming rod formed as a tube. This can serve as an additional aiming aid for the actual medical instrument.

In a further embodiment of the invention, the arcuate element has an angle scale.

This makes it possible to ascertain or document the precise angular position, on the circularly arcuate element, of the shaft of the medical instrument in relation to the longitudinal axis of the aiming rod.

In a further embodiment of the invention, the medical instrument is formed as an arthroscope.

The advantage of this measure is that, by using an arthroscope, which has an optical system in the shaft, the entire joint can be inspected from the inside and, if necessary, an intervention can be performed.

After the removal of the partial aiming device, tubes for the introduction of a sterile liquid into the joint or aspiration can be attached to the arthroscope at its LUER connector.

It goes without saying that the features mentioned above and those still to be explained below can be used not only in the stated combinations but also in other combinations or on their own without going beyond the bounds of the present invention.

BRIEF DESCRIPTION OF THE DRAWINGS

The invention is described and explained in greater detail below with the aid of a selected embodiment example in conjunction with the drawings.

FIG. 1 shows a lateral view of a partial aiming device according to the invention, FIG. 2 shows another lateral view of the device according to the invention presented in FIG. 1.

DETAILED DESCRIPTION OF PREFERRED EMBODIMENTS

Figure 3:
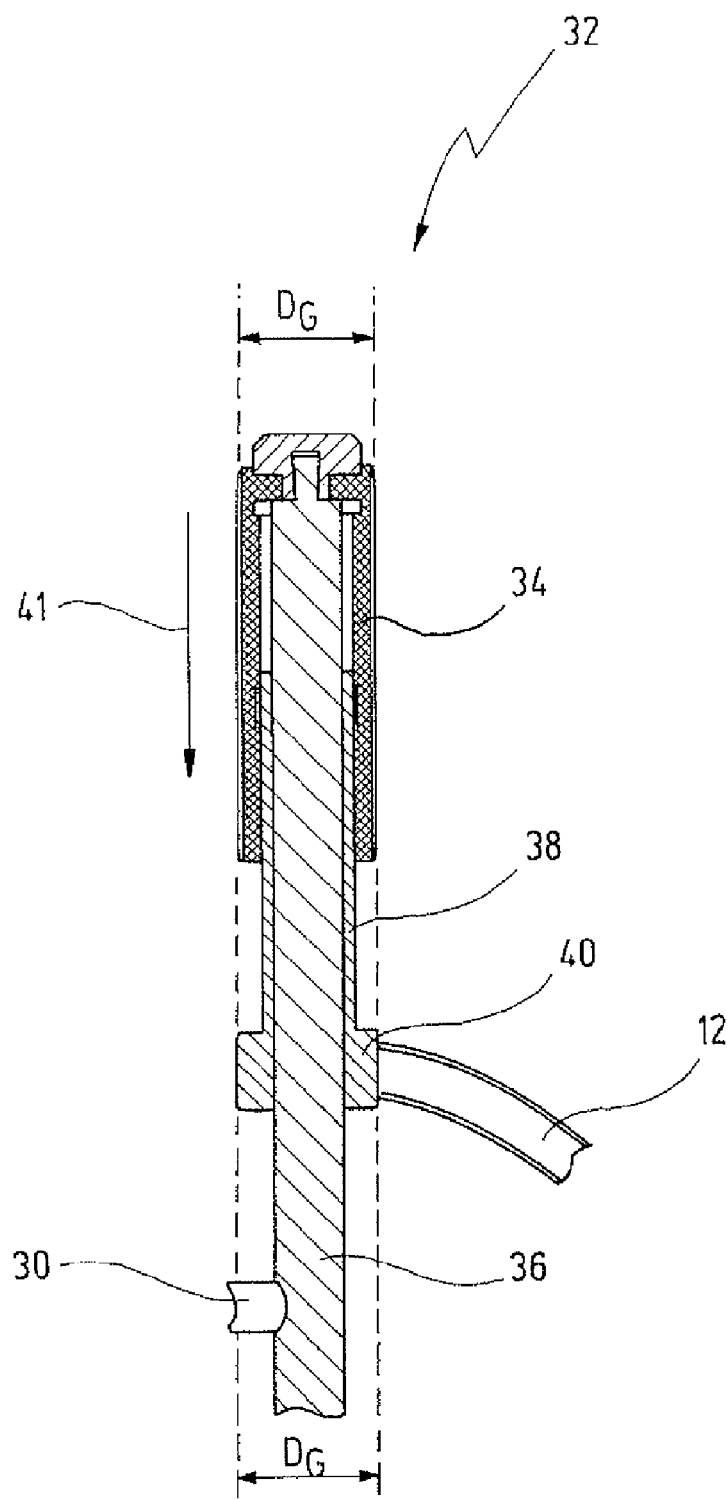
FIG. 3 shows a section along a longitudinal axis of an adjusting device.

A partial aiming device for targeting an arthroscopic operation site for a medical intervention or an investigation, shown in the figures, is as a whole referred to by the reference number 10.

The partial aiming device 10 shown in FIG. 1 has a circularly arcuate element 12. The arcuate element 12 has an angle scale 13.

On the circularly arcuate element 12 there is mounted a first, radially extending aiming rod 14 via a fitting wheel 16.

The first aiming rod 14 can be moved back and forth along the circularly arcuate element 12 by means of the fitting wheel 16. The first aiming rod 14 extends radially with respect to a circular arc of the circularly arcuate element 12 in all slide positions.

The fitting wheel 16 is connected to the arcuate element 12, the purpose of which is to permit the movement and to fix the aiming rod 14 in a specific position on the circularly arcuate element 12.

In this embodiment, the first aiming rod 14 is shown as a tube 18 which has a lumen running through it. Through this lumen of the tube 18 it is possible to pass, for example, a puncture needle to be inserted into the joint.

Figure 4:
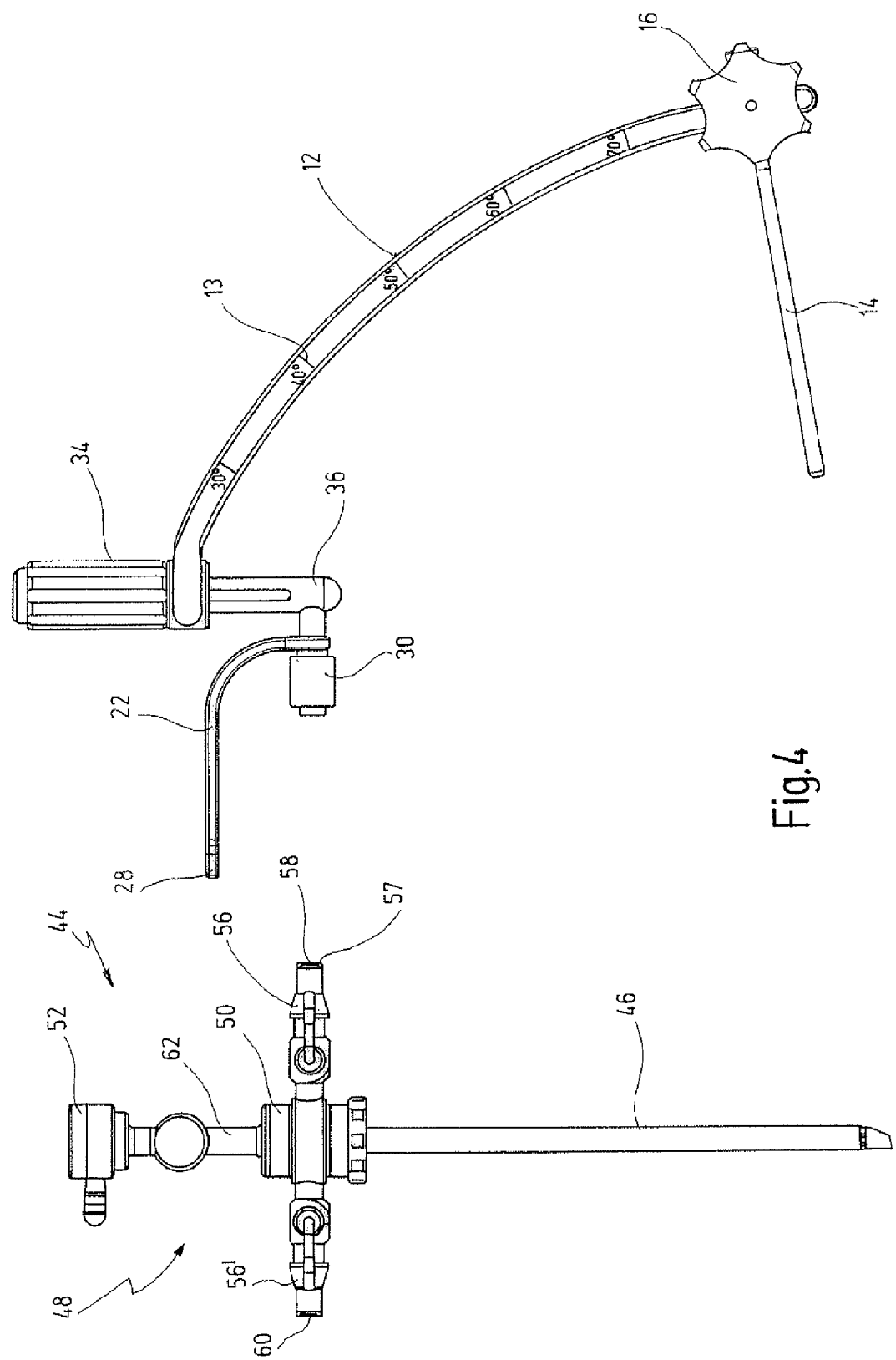
FIG. 4 shows the partial aiming device according to the invention in a lateral view which is similar to that presented in FIG. 1 and which shows a medical instrument not yet attached to the partial aiming device.
Figure 5:
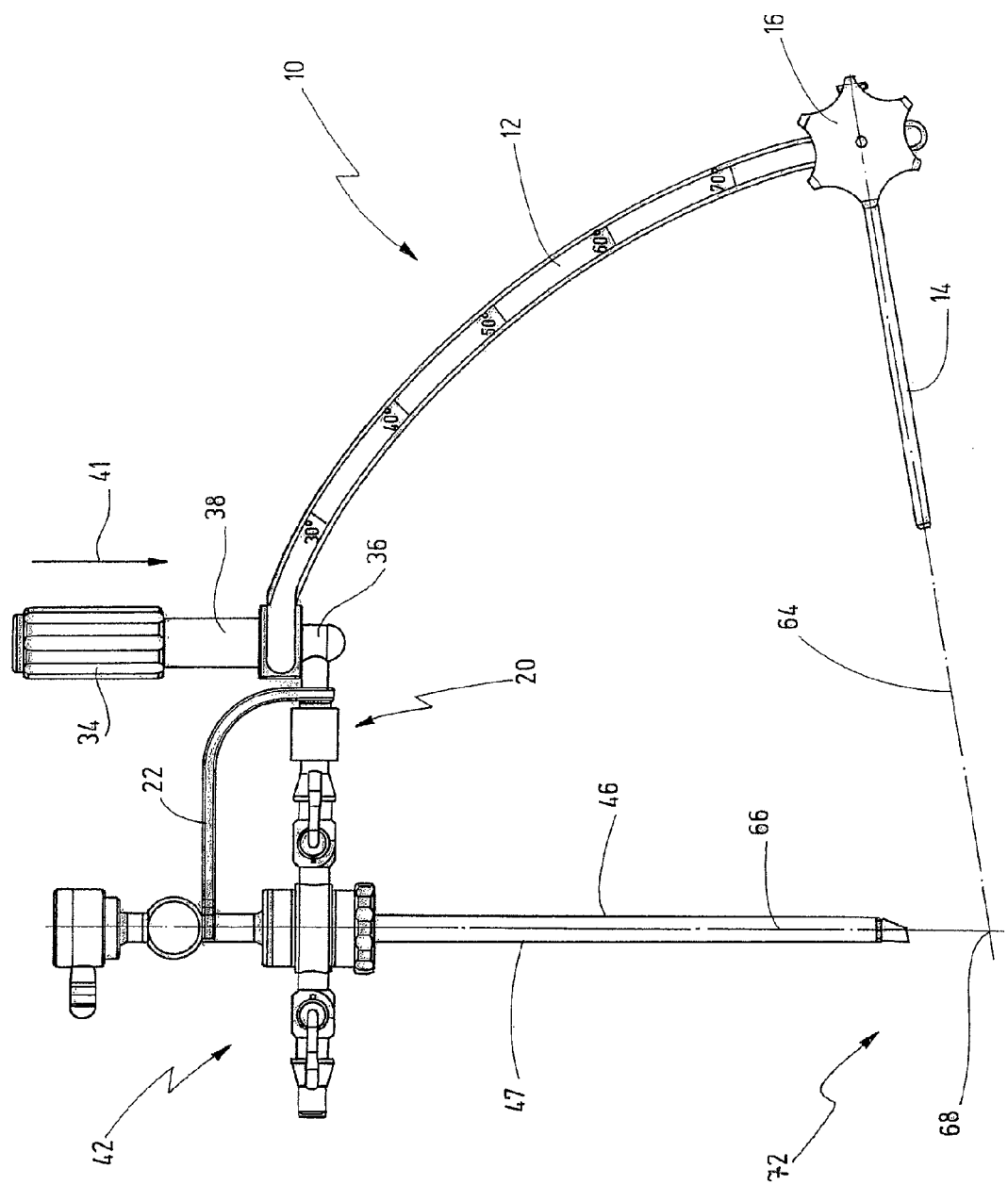
FIG. 5 shows the medical instrument attached to the partial aiming device.
Figure 6:
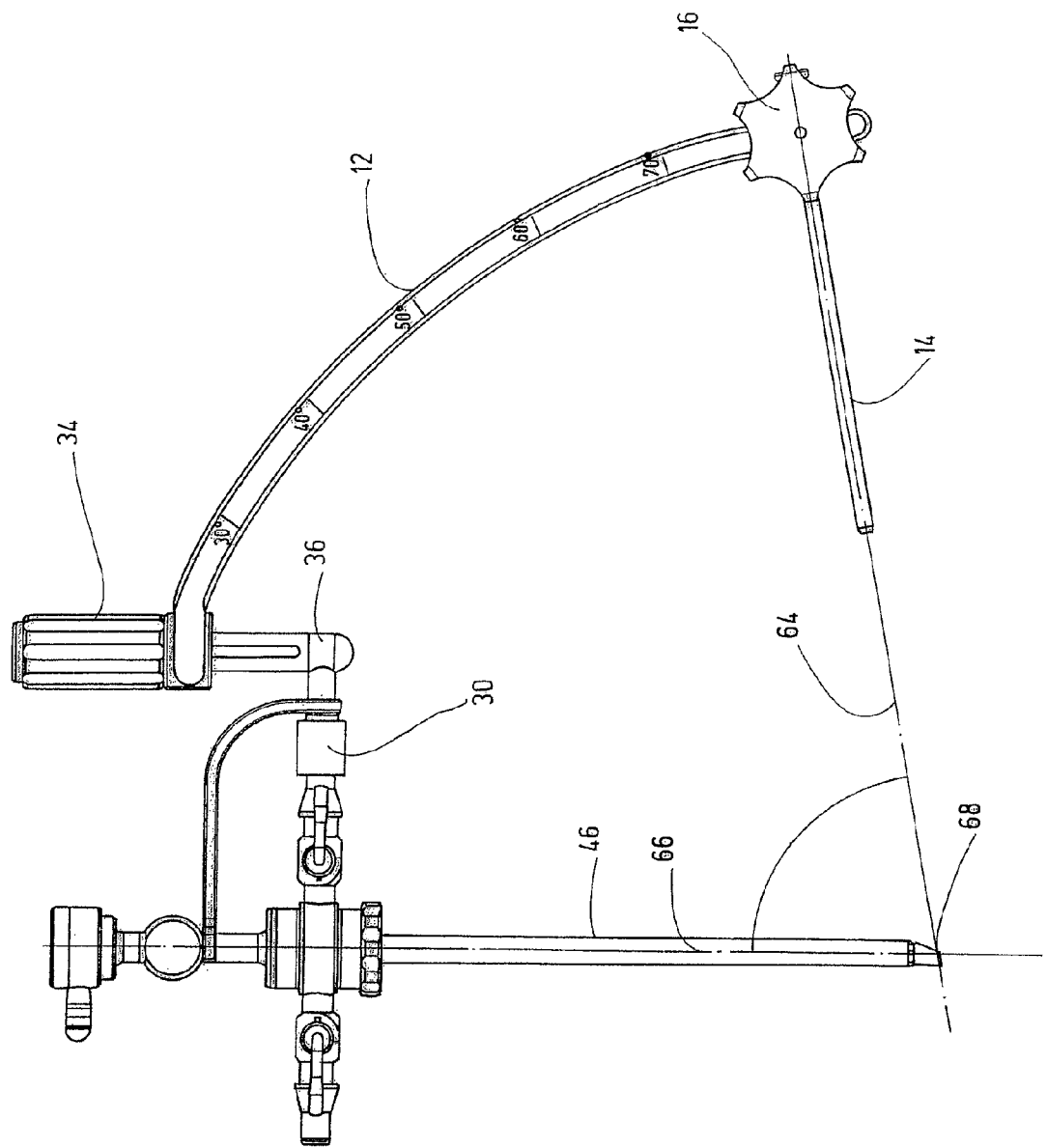
FIG. 6 shows the assembly of the medical instrument of FIG. 5 with the adjusting device in an advanced position.

The circularly arcuate element 12 has a connecting device 20, which serves to connect the partial aiming device 10 according to the invention to a medical instrument 42, which is shown in FIGS. 4 to 6.

The connecting device 20 has a bracing arm 22 to support the medical instrument 42. A first end 24 of the bracing arm 22 is firmly connected to the connecting device 20.

A second end 26 of the bracing arm 22 serves to effect a form-closure with the medical instrument 42 and is formed as a fork-shaped element 28, as can be specifically seen in the diagram in FIG. 2.

The connecting device 20 has a connector 30 which is designed so that the latter can be attached to an existing connecting site of the medical instrument 42. The design of the connecting site of the medical instrument 42 is explained in greater detail in connection with FIGS. 4 to 6.

The connecting device 20 is in addition provided with an adjusting device 32 by means of which the connecting device 20 can be moved radially in the plane of the arcuate element 12.

The adjusting device 32, which is located at one end of the circularly arcuate element 12, has a rod-shaped rotatable handle 34.

The outside of the handle 34 has a pattern of notches 35 that allows the adjusting device 32 to be held firmly and securely by the human hand.

A detailed design of the adjusting device 32 is shown in FIG. 3.

Within the handle 34 there is a rod 36, which is firmly connected to the handle 34. The rod 36 end which projects from the handle 34 is firmly connected to the connector 30, of which only the initial portion is shown in this diagram.

Between the handle 34 and the rod 36 there is a tube 38.

The rod 36 can be moved linearly in the tube 38 by means of a longitudinal groove 37 and a corresponding projection.

In FIG. 3, the adjusting device 32 is in a partially retracted position, which can be defined by the distance between the handle 34 and a step 40 of the tube 38. If the handle 34 is turned in one direction, the tube 38 is clamped between the handle 34 and the rod 36, and the adjusting device is locked. Turning the handle 34 in the opposite direction releases the lock, and the adjusting device 32 can be moved along the rod 36, as exemplary indicated for one direction by arrow 41.

FIGS. 4 and 5 show how a medical instrument 42 is attached to the partial aiming device 10 according to invention.

The medical instrument 42 shown in FIG. 4 is formed as an arthroscope 44.

The arthroscope 44 has a shaft 46, which serves to accommodate an optical system. The shaft 46 is connected to a head 48, which has a housing 50 and a terminal eyepiece 52. It also has an irrigation/suction device 56, to which two tubes can be connected. Liquid is introduced into the joint through one tube and aspirated through the other.

The irrigation/suction device 56 has two connectors 58 and 60, which are designed as LUER connectors.

The connector 30 of the connecting device 20 is attached to one of the existing connecting sites 57 of the arthroscope 44, this connecting site here being formed as a LUER connector 58.

The second end 26 of the bracing arm 22 is formed as a fork-shaped element 28, which fits round the arthroscope neck 62 and is supported on it.

FIG. 5 shows the arthroscope 44 attached to the partial aiming device 10 according to the invention.

The connector 30 is connected to the LUER connector 58 and the fork-shaped element 28 surrounds the neck 62 of the arthroscope 44. The partial aiming device 10 rests at two sites at the arthroscope 44.

It can be seen that the shaft 46 of the arthroscope 44 extends radially to the first aiming rod 14. It thus serves as a second aiming rod 47.

In this attached state, the longitudinal axis 64 of the first aiming rod 14, which is formed as a tube 18, and a longitudinal axis 66 of the arthroscope 44 intersect at a point of intersection 68 which corresponds to the site to be targeted.

To bring a distal end 72 of the shaft 46 of the arthroscope 44 as close as possible to the point of intersection 68 of the longitudinal axes 64 and 68, the adjusting device 32 is released and the distal end of the shaft 46 is brought up against the joint and, after verification of the correct position, introduced into this aiming instrument. This situation is shown in FIG. 6.

In this position, a puncture cannula aiming at the distal end of the arthroscope shaft 46 can be inserted through the first aiming rod 14 formed as a tube 18.

Once the puncture cannula has been brought to the desired position in the joint, the shaft 46 of the arthroscope 44 can be inserted into the joint, with the aid of a trocar thorn if necessary.

Once the arthroscope 44 is accurately in situ, the partial aiming device 10 can be removed. For it, the connector 30 of the connecting device 20 is released from the LUER lock 58 of the arthroscope, for example by turning the connector 30 about 180°. The partial aiming device 10 can be removed from the arthroscope 44 and consequently from the operation site. Subsequent manipulations on the joint are then no longer impeded by the arcuate element 12 and the first aiming rod 14.

What is claimed is:

1. A partial aiming device for targeting an arthroscopic operation site for a medical intervention, comprising
   a circularly arcuate element,
   a first aiming rod extending radially from said circularly arcuate element, said first aiming rod can be moved along said circularly arcuate element,
   a connecting device arranged at said circularly arcuate element, said connecting device is designed for connecting a medical instrument having a shaft in such a way at said circularly arcuate element that said shaft of said medical instrument extends radially from said circularly arcuate element too, said shaft being oriented by said connecting device as a second aiming rod that extends towards said first aiming rod,
   a bracing arm for supporting said medical instrument, said bracing arm having a first end and second end, said first end of said bracing arm firmly connected to said connecting device and said second end of said bracing arm can be brought against said medical instrument in such a way to effect a form-closure,
   wherein said connecting device is designed in that it can be attached to an existing connecting site of said medical instrument having a well-defined location on said medical instrument apart from said shaft of said medical instrument, allowing to remove the partial aiming device from said medical instrument when said shaft of said instrument is inserted into an arthroscopic operation site, and
   wherein said existing connecting site of said medical instrument is formed as a LUER connector.

2. The partial aiming device of claim 1, wherein said connecting device is provided with an adjustment device by means of which said connecting device can be moved axially in a direction of an extension of said shaft of said medical instrument.

3. The partial aiming device of claim 1, wherein an angle between a longitudinal axis of said first aiming rod and a longitudinal axis of said shaft of said medical instrument when attached is approximately 30° to 80°.

4. The partial aiming device of claim 1, wherein said first aiming rod is designed as a tube.

5. The partial aiming device of claim 1, wherein said circularly arcuate element has an angle scale.

6. The partial aiming device of claim 1, wherein said medical instrument is an arthroscope.

* * * * *